United States Patent [19]

Dudek

[11] Patent Number: 4,935,000

[45] Date of Patent: Jun. 19, 1990

[54] EXTRACELLULAR MATRIX INDUCTION METHOD TO PRODUCE PANCREATIC ISLET TISSUE

[75] Inventor: Ronald W. Dudek, Greenville, N.C.

[73] Assignee: East Carolina University, Greenville, N.C.

[21] Appl. No.: 46,040

[22] PCT Filed: Mar. 27, 1987

[86] PCT No.: PCT/US87/00655

§ 371 Date: Apr. 27, 1987

§ 102(e) Date: Apr. 27, 1987

Related U.S. Application Data

[63] Continuation-in-part of Ser. No. 847,413, Apr. 3, 1986.

[51] Int. Cl.$^5$ .............................................. A61B 19/00
[52] U.S. Cl. ..................................... 600/36; 128/898; 435/1
[58] Field of Search .................... 604/891.1, 890.1, 27, 604/28, 93; 623/11; 435/1; 424/110; 514/866; 600/36; 128/897, 898

[56] References Cited

U.S. PATENT DOCUMENTS

| | | | |
|---|---|---|---|
| 4,439,521 | 3/1984 | Archer | 435/240.23 |
| 4,505,266 | 3/1985 | Yannas et al. | 128/898 |
| 4,609,551 | 9/1986 | Caplan et al. | |
| 4,642,120 | 2/1987 | Nevo et al. | |
| 4,642,292 | 2/1987 | Raid et al. | |
| 4,645,669 | 2/1987 | Reid | 435/1 |
| 4,673,566 | 6/1987 | Goosen et al. | 424/110 |
| 4,678,670 | 7/1987 | Tomic | 514/866 |
| 4,696,286 | 9/1987 | Cochrum | 435/1 |
| 4,727,018 | 2/1988 | Eichner et al. | 435/240.1 |
| 4,829,087 | 5/1989 | Ammon | 514/866 |

OTHER PUBLICATIONS

Kusakale, et al., "Early Development of Mouse Anterior Pituitary", Biol. Abstr., 79(1):AB-191, 1984.
Paranko et al., "Epithelial & Mesenchymal Cell Differentiation", Developmental Biology, vol. 117, pp. 135–146 (1986).
Sakaguchi et al., "Earlier Appearance of Murine Mammary Tumor Virus", Biol Abst 73(11):8023.
Sun et al., "Artificial Endocrine Pancreas", Diabetes, vol. 26, No. 12, pp. 1136–1139, (1977).
Golowow, Nikolas and Grobstein, Clifford, "Epitheliomesenchymal Interaction in Pancreatic Morphogenesis", Developmental Biology, 4, 242–255 (1962).
"Persistence of Responsiveness of Adult Mouse Mammary Gland to Induction by Embryonic Mesenchyme", Sakakura, Sakagami and Nishizuka, Developmental Biol. 72, 201–210 (1979).
"Acceleration of Mammary Cancer Development by Grafting of Fetal Mammary Mesenchymes in C3H Mice", Sakakura, Teruyo, Sakagami, Yasuo, Nishizuka, Yasuaki, Gann, 70, 459–466, Aug. (1979).
Ekblom et al. entitled: Organogenesis in a Defined Medium Supplemented With Transferrin from Cell Differentiation, 10 (1981) 281–288 Elsevier/North–Holland Scientific Publishers, Ltd.
Biological Abstracts 83(9):AB-366, Ref. No. 85037, Schechter et al, Rathke's Pouch Grafts in Adult Brain Sites, American Journal of Anatomy 178(1): 55–64 (1957).

Primary Examiner—Stephen C. Pellegrino
Assistant Examiner—Sharon Rose
Attorney, Agent, or Firm—Sarah E. Bates; Paul C. Flattery; Marjorie D. Hunter

[57] ABSTRACT

A method and composition of regenerating tissue. More specifically, a method for regenerating pancreatic islet tissue having the histological and insulin-containing properties of islets typically found in neonatal or adult animals is described. The regenerated islet tissue is produced by fetal mesenchyme acting upon an epithelium such that an inductive message causes the epithelium to differentiate into islet tissue.

9 Claims, 2 Drawing Sheets

EXTRACELLULAR MATRIX INDUCTION METHOD TO PRODUCE PANCREATIC ISLET TISSUE

This application is a continuation-in-part of U.S. Ser. No. 847,413 filed Apr. 3, 1986.

BACKGROUND OF THE INVENTION

Embryonic development of the pancreas involves an epithelial endoderm budding from the primitive gut tube into surrounding mesenchyme (splanchnic mesoderm). The process is described in detail in the publication by R. Pictet and W. Rutter, HANDBOOK OF PHYSIOLOGY, Vol. 1, Section 7, Endocrinology: Endocrine Pancreas, D. Steiner and N. Freinkel, eds., Amer. Physiol. Soc. L972, pp. 25–66. The sequential epithelial/mesenchymal interactions results in the formation of both exocrine and endocrine pancreas. Later in adult life, it is believed that very little endocrine neogenesis occurs in the pancreas. This has led to the conclusion of some investigators in the diabetes field to consider the beta cell (the beta cell is the source cell for insulin) a "terminal" cell. A terminal cell is a fully differentiated cell that exhibits very little mitosis in adult life, and consequently, at birth, an individual has the full complement of these cells. The terminal nature of the beta cell has far reaching implications in the field of diabetes since beta cell destruction or functional impairment results in a devastating clinical situation without any hope of new, healthy, beta cell formation occurring to alleviate the disease.

In the past, many investigators have studied the effects of various conditions on the mitotic activity of pre-existing beta cells in the pancreas. These conditions have included the effect of diet, hormones, partial pancreatectomy, diabetogenic chemicals, genetic manipulation, sulfonylureas, insulin antibody, glucose, and amino acids. See, for example, J. Logothetopoulos, HANDBOOK OF PHYSIOLOGY, Vol. 1, Section 7, Endocrinology: Endocrine Pancreas, D. Steiner and N. Freinkel, eds., Amer. Physiol. Soc. 1972, pp. 67–76. The crux of these studies has been to increase the mitotic activity of pre-existing beta cells. None of these studies has dealt with the concept of the neoformation or regeneration of islet beta cells from non-islet entities (islets are groups of beta cells).

Many investigators have found that in vitro culture of fetal pancreas exhibits a high rate of beta cell mitosis and also some evidence of neoformation of beta cells from "budding islets" which seems to result from true neogenetic process (morphogenesis and histogenesis); et al., Morphological Study of Cultured Pancreatic Fetal Islets: Diabetes, Vol. 29, Jan. 1980, pp. 16–21. In addition, Archer and Jai (U.S. Pat. No. 4,439,521; Mar. 27, 1984; Method for Producing Self-Reproducing Mammalian Pancreatic Islet-like Structures) describe a method for producing pancreatic islet-like structures using in vitro culturing techniques. They have been able to increase islet tissue using standard tissue culture technology of pancreatic islets, pancreatic duct pieces, cell clusters of pancreas, cell tissues obtained as by products of the culturing method, or previously produced islet-like structures.

The invention of this application relates to a method and composition for regenerating cells in a post natal subject, cells which do not normally regenerate apart from fetal development. Specifically, islet cells of the pancreas may be regenerated.

SUMMARY OF THE INVENTION

In accordance with this invention, a method is provided which comprises implanting into a living subject an effective amount of fetal mesenchyme cells of a type and age capable of eliciting a desired biological response from other fetal cells. As the result of such implantation, the biological response is elicited in the cells of the living subject. Thus, by this method, cells in the body of an adult may be stimulated by the implantation of the proper mesenchyme cells to behave in a manner which is abnormal for adult cells, but which is typical behavior for precursor cells to those adult cells in the fetus. By this technique, desired growths and transformations of living adult cells can take place in a manner which is analogous to fetal growth; specifically, the process involves reawakening dormant adult "precursor" epithelial cells by use of temporally spacially limited fetal mesenchyme.

For example, new pancreatic islet cells which secrete insulin have been formed in accordance with this invention from ductal epithelial cells of the pancreas, thus providing hope for a cure of diabetes in patients by means of this invention. Another hopeful possibility that may be accomplished by the method of this invention is the eliciting of nerve cell regrowth to repair nerve damage in patients by the use of an appropriate selection of fetal mesenchyme cells. Also, wound healing may be stimulated, with epidermal regeneration, for example. Small body structures such as parts of the eye, heart, or inner ear may hopefully be regrown in postnatal subjects by this invention.

Mesoderm (source of this mesenchyme) is that tissue which derives its origin from the middle layer of the early embryo. It has been previously observed that, during the development of the embryo, mesenchyme at various times exerts an influence on other cells to cause the other cells to multiply and/or transform into new tissues in a manner which appears to be induced by the mesenchyme.

In accordance with this invention, the broad concept is to select and implant mesenchyme from a fetus of the exact type and the exact age at which such cells are exerting their influence on nearby fetal epithelial cells to exhibit a normal biological response as another step in the development of the fetus. For example, the formation of islet cells out of pancreatic ductal epithelium, or the growth of nerves, are two possibilities for biological responses that appear to be governed by certain fetal mesenchyme tissues at certain times in the normal development of the fetus. By this invention, the very fetal mesenchyme which elicits such a response from other tissues is thus transplanted into a post-fetal living subject, with the fetal mesenchyme being transplanted into a site in the patient where they can survive for a long time enough to perform their influence on tissues of the living subject, which tissues are preferably adjacent the transplantation site.

Alternatively, equivalent to mammalian fetal mesenchyme include tissue from lower animal forms on the phylogenetic scale that have known regenerative capability, such as salamander, lizard, or crayfish, for example for limb regeneration.

As stated above, it has been found that new pancreatic islet cells can be formed from ductal epithelium in adult living subjects (specifically rats) and that such islet cells can function normally to suppress symptoms of diabetes in such subjects.

Specifically, the fetal mesenchyme used herein may comprise pancreatic bud tissue from a fetus, (composed of fetal mesenchyme plus fetal epithelium) or, alternatively, fetal mesenchyme cells from an 11 to 14 day old fetus, i.e., those particular cells which are believed by embryologists to have a role in the formation of the pancreatic islet cells in the rat fetus.

Additionally, fetal mesenchyme may be implanted while in recombinant, a relationship of fetal mesenchyme with adult epithelial cells of the living subject which are capable of exhibiting the biological effect as elicited by the fetal mesenchyme. The fetal mesenchyme is isolated at such time in development when the inductive activity of the mesenchyme is available. Specifically, 11 to 14 day old rat fetus mesenchyme may be formed into recombinants with pancreatic adult ductal epithelial tissue. After the recombinant tissue body has formed, they may be transplanted subcutaneously into a nude mouse, creating a living cell body in the mouse that forms insulin-containing beta cells.

The location of the implantation is preferably adjacent to the cells of the living subject in which the biological response is to be elicited. Accordingly, where nerve regrowth is desired, the implantation should take place at the injury site, from which scar tissue is preferably cleared away to provide an open path for the nerve regrowth and rejoining. In the instance where it is desired to form new islet tissue in the pancreas, the fetal mesenchyme may be implanted in the omentum of the living subject. The importance of where fetal mesenchyme is implanted raises the distinct possibility of an inducting, trophic, and/or mitogenic factor being secreted from the mesenchymal tissue. This factor could be isolated and injected into the individual directly without the need to implant the cellular mesenchymal component. Consequently, this invention additionally directs itself towards regenerating pancreatic islets by injecting an isolated mesenchymal factor.

The present invention is also directed toward a method to cause the neo-formation or regeneration of pancreatic islet tissue or other tissues using the induction capacity of an extracellular matrix upon a ductal epithelium. The extracellular matrix is isolated at such time in development when the inductive activity of the mesenchyme is available. One purpose of the method is to provide a treatment for diabetes by replacing beta cells that have either been destroyed or are functionally impaired. The method is unique in that all diabetics have ductal epithelium in their pancreas that is capable of being induced by an extracellular matrix to produce islet tissue.

A further purpose of the invention is to cause neoformation or regeneration of pancreatic islet tissue that is histocompatible with the diabetic patient so that no immune response or rejection occurs when the regenerated islet tissue is subsequently transplanted back into the diabetic patient. Present transplantation procedures for the treatment of diabetes have the rejection of the transplanted islet tissue as a major obstacle to overcome. The described method minimizes the issue of immune rejection since the regenerated islet tissue comes from the diabetic patient's own epithelium and consequently should have the same genotype and/or histocompatible antigens, thus alleviating the immune response.

The method described herein differs from previous attempts to increase islet beta cell numbers by (a) employing the use of fetal mesenchyme acting upon an epithelium in order to redirect the differentiation process in a manner that results in the neoformation of islet tissue and (b) using a non-islet entity ductal epithelium from which to regenerate the islet tissue.

BRIEF DESCRIPTION OF THE DRAWINGS

The invention will be better understood by reference to the following detailed description when considered in connection with the accompanying drawings wherein.

DETAILED DESCRIPTION OF THE INVENTION

Figure 1:
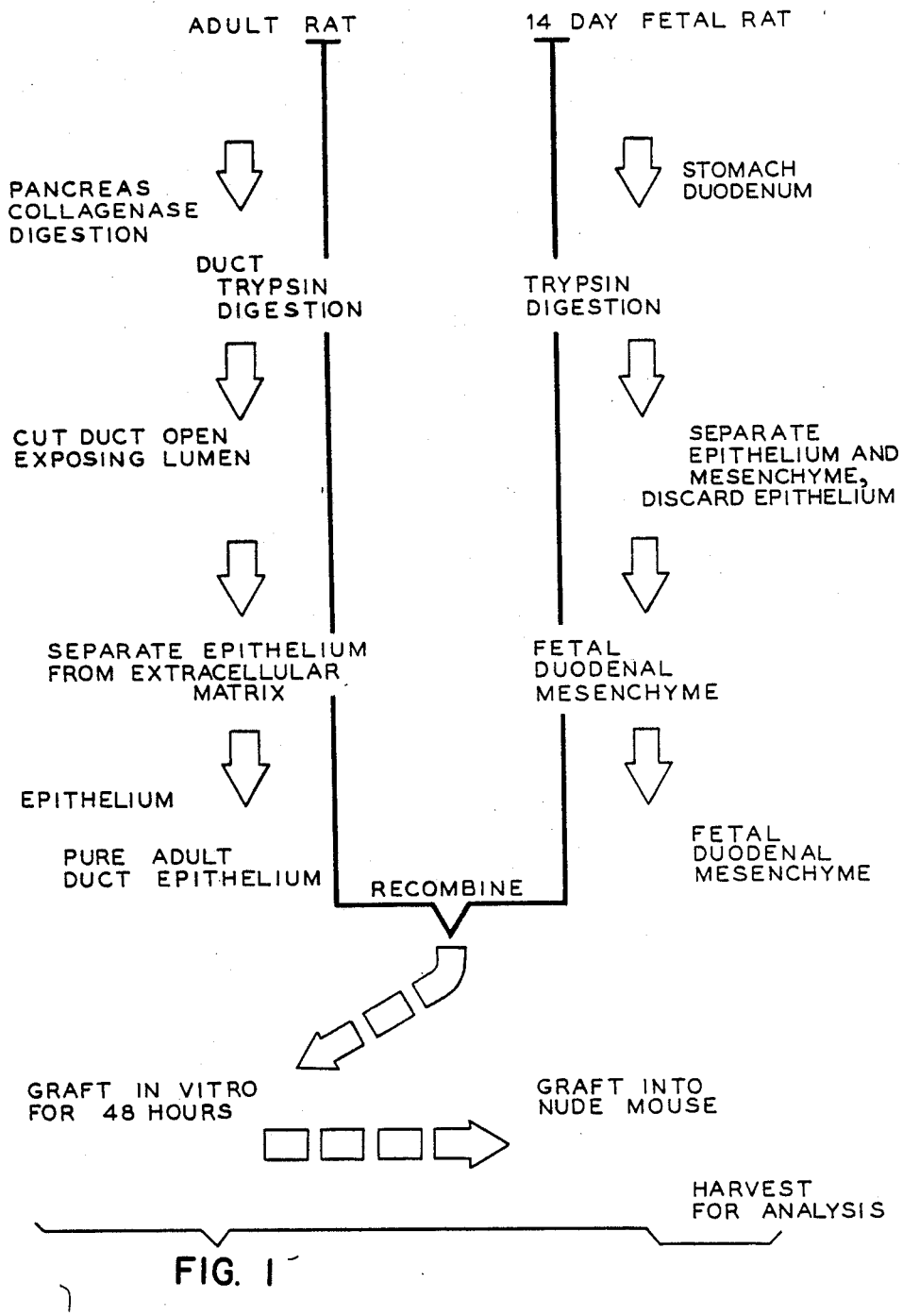
FIG. 1 is a schematic flow diagram of a method of producing regeneration of pancreatic islet tissue.

A specific embodiment of the present invention involves the interaction of an extracellular matrix, such as fetal mesenchyme with a pancreatic ductal epithelium to produce pancreatic islet tissue. It is applicable, however, to any tissue having a ductal element and contemplates using a patient's own tissue as a source of transplantable differentiated tissue. The extracellular matrix or mesenchymal can be obtained from a fetal source, a lower phylogenetic source, or from chemically defined material, isolated from biological sources, chemically synthesized or genetically engineered.

More specifically, in a method of producing pancreatic islet tissue, the method of the invention involves the recombination of substantially pure adult ductal epithelium with fetal duodenal mesenchyme as the extracellular matrix. Mesenchyme is an embryonic tissue consisting of mesenchymal cells and an extracellular matrix which is composed of fibers, proteins, proteoglycans and glycosaminoglycans. The mesenchymal cells are supported in the extracellular matrix of the mesenchyme. An extracellular matrix may consist of any or all of the following: a protein lattice network, differentiation factors secreted by cells or tissues involved in directing such differentiation, or cells or tissues which, by virtue of cell to cell contact, direct differentiation.

Although it is hypothesized that a pool of islet precursor cells exists throughout life, it is believed that the islet cytodifferentiation from pancreatic ductal epithelium by means of the described method is a consequence of a true reawakening of fetal differentiation. It has been determined that the presence of a substantially pure pancreatic ductal epithelium is essential for islet cytodifferentiation to occur. Any residual adult stroma adhering to the epithelium was found to prevent cytodifferentiation. It is believed the adherent adult stroma acted as a barrier and inhibited interaction between fetal mesenchyme and adult epithelium, thus preventing cytodifferentiation. Even if an islet progenitor cell population is present in adult ductal epithelium, islet renewal does not significantly occur in the adult. Electron dense cells, considered to be endocrine progenitors, occur in ducts of developing pancreas, but no such cells have been observed in adult pancreatic ductal epithelium. Since only epithelium stripped cleanly from adult stroma ("substantially pure epithelium") was recombined with mesenchyme, the chance of pre-existing islets attached to the periphery of the duct contaminating the epithelium is minimal.

The invention further provides a method of preparing substantially pure epithelium, facilitating the removal of adult stroma which could block tissue differentiation as well as a method of identifying and preparing adult ductal epithelium suitable for use in tissue recombination.

The interaction of extracellular matrix and ductal epithelium can occur in vitro or in vivo under conditions necessary for growth and/or maintenance of the mammalian cells. An in vitro culturing system would consist of a medium, serum, serum substitute and/or other ingredients to promote the growth and maintenance of mammalian cells. The culturing system may consist of a vessel treated with a variety of substances that will create a lattice or environment on which the interaction and/or regeneration of islet tissue may occur. In vivo, a transplantation site into a human or animal would serve to supply the nutrients, gases, blood, nerve supply, and any other ingredients necessary for the growth or maintenance of mammalian cells. The human or animal may be a nondiabetic or diabetic host.

The human or animal donating the epithelium to be induced by the extracellular matrix to produce pancreatic islet tissue may then be transplanted back with the regenerated islets, and the islets will be functional and substantially free from immune rejection.

EXAMPLE 1

The method for the regeneration of pancreatic islet tissue using an extracellular matrix and epithelium can be described as follows and with reference to the flow diagram of FIG. 1. A pure adult rat ductal epithelium was isolated by digesting the chopped adult rat pancreas with collagenase (3 mg/pancreas) in Hank's buffered saline salt solution, pH 7.4, containing 0.02% fat-free BSA, 0.01% soybean trypsin inhibitor, and 0.5% EDTA. The pancreas was shaken for 15 minutes at 37 degrees C. or incubated without shaking for one hour at 4 degrees C. Subsequently, both large and small ducts were picked from the chopped digested tissue and incubated in 1% Diffco trypsin in Hank's buffered salt solution (no additions) for one hour at 4 degrees C. The duct was cut open and the epithelium carefully stripped away from the surrounding connective tissue thereby obtaining a "pure" epithelium.

The extracellular matrix used in this method was derived from fetal mesenchyme. The fetal mesenchyme was isolated by dissecting the 14-day rat fetus in 20% fetal bovine serum (FBS) and incubating the stomach-duodenal portion in 1% Diffco trypsin for 3 hours at 4 degrees C. After incubation, the trypsin solution was removed and 50% FBS was added. After combining the fetal mesenchyme and epithelium together (hereafter termed recombinant), the recombinant was placed in a 95% air/5% $CO_2$ humidified atmosphere at 37 degrees C. for 48 hours on a 1% bactoagar gel culture containing RPMI 1640 culture medium. The recombinant was marked with bone charcoal to aid in recovery and transplanted subcutaneously into a nude mouse for a six-week period. Mesenchyme alone, ductal epithelium alone, intact fetal pancreatic bud, and isolated adult pancreatic islets were also transplanted into other nude mice as controls. After six weeks, transplanted tissue was harvested and (a) fixed in Bouin's for light microscopy and immunocytochemistry, (b) fixed in 2% paraformaldehyde-2.5% glutaraldehyde in 75 mM cacodylate buffer for one hour on ice followed by. 1% osmium tetroxide in 100 mM cacodylate buffer for electron microscopy, or (c) sonicated and extracted in acid ethanol for 24 hours at 4 degrees C. for radioimmunoassay of insulin. No tissue other than the transplanted tissue was analyzed.

A total of 57 recombinants were processed. Twelve of 23 (52%) contained immunoassayable insulin; 10 out of 17 (59%) showed by light microscopy histological evidence of extracellular matrix/epithelium activation with development of islets; and 3 of the above 10 (30%) were confirmed to be islets as indicated by the presence of insulin-containing beta cells. The remaining 17 recombinants were processed for electron microscopy and they indicated intimate association of the extracellular matrix with the epithelium, thus producing pancreatic islet tissue.

The range of weights and insulin content of the harvested tissue are recorded in Table 1. The weight and insulin content of the transplanted tissue were highly variable and probably reflects the amount of tissue that was originally isolated and transplanted. Extracts of 12 recombinants were assayed at various dilutions and the insulin content was found to be parallel with the standard curve for rat insulin.

Light microscopic evaluation of the recombinants showed clusters of cells closely resembling islet tissue and containing insulin immunoreactivity as indicated by immunocytochemistry. Electron microscopic analysis of the recombinants demonstrated an interaction between the extracellular matrix and the epithelium which seems to be a hallmark for islet tissue regeneration in this method and cells containing secretory granules typical of islet beta cells.

TABLE 1

| Transplanted Tissue | N | Wet Weight (mg) Range | Insulin (ng/mg of Tissue) Range |
|---|---|---|---|
| Recombinants | 12 | 1.1–15.4 | 0.11–20.4 |
| Islets | 7 | 4.8–20.0 | 0.01–2.67 |
| Pancreatic bud | 3 | 0.8–17.1 | 0.05–11.9 |
| Mesenchyme | 7 | 0.5–13.7 | 0* |
| Duct | 6 | 0* | 0** |

*No insulin detectable by RIA
**No identifiable transplanted tissue could be recovered for weight and extraction after 6 weeks.

EXAMPLE 2

Figure 2:
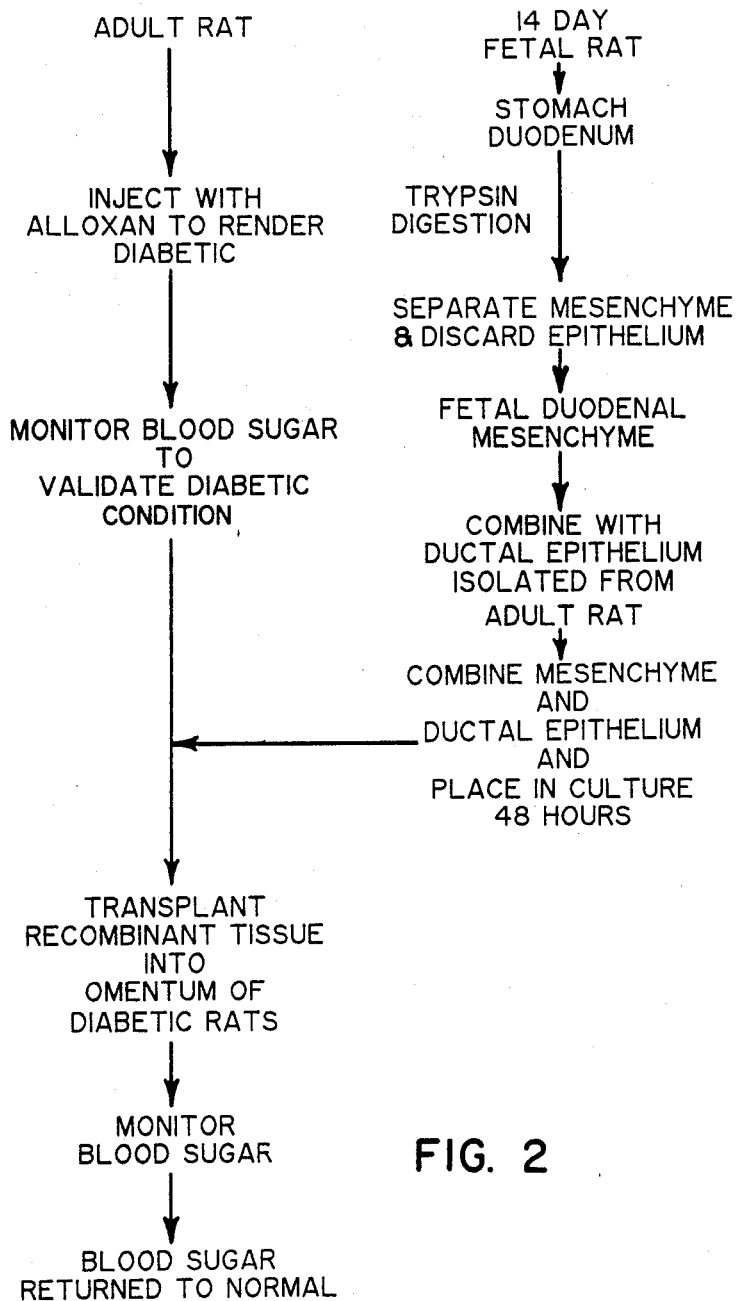
FIG. 2 is a schematic flow diagram of a method of producing regeneration of pancreatic islet tissue in situ.

This example is directed toward a method of in situ regeneration of islet tissue by transplanting recombinant tissue into an appropriate transplantation site. This method for regeneration of pancreatic islet tissue can be described as follows and with reference to the flow diagram of FIG. 2.

A diabetic colony of Sprague-Dawley rats was established by injecting 50 mg/kg body weight of alloxan intravenously. The blood glucose values were monitored periodically to document the hyperglycemic condition. All rats had elevated blood glucose values for a least one week before receiving a transplant.

Four noninbred alloxan diabetic rats have been transplanted with recombinant tissue made in the manner of Example 1. The tissue was implanted into the omentum of each rat. After such transplantation, all four of the diabetic rats showed normalization of blood glucose levels within seven days of the transplantation. In addition, both serum insulin and in situ pancreas insulin levels were elevated in comparison to a control diabetic rat. Thus, it appears that the above process resulted in the creation of new islet cells in the rats which resulted in the alleviation of their diabetes. Furthermore, after 10 days, the transplant was removed again from the diabetic rats with the results shown with respect to days 14 and 16.

The results of this experiment are summarized in Table II below.

TABLE II

| Rat # | Days after Transplantation | | | | | Insulin Levels Found in: | | |
|---|---|---|---|---|---|---|---|---|
| | 1* | 7 | 10** | 14 | 16 | ng/ml Serum | ng/mg In situ Pancreas | ng/ml Recomb Tissue |
| | Blood Glucose mg/dl | | | | | | | |
| 51 | 386 | 71 | 97 | 86 | 85 | 19.6 | 52.1 | 2.2 |
| 52 | 369 | 77 | 145 | 109 | 85 | 7.9 | 54.3 | 17.4 |
| 53 | 370 | 167 | 158 | 89 | 183 | 5.6 | 42.5 | *** |
| 54 | 496 | 80 | 76 | 112 | 142 | 4.1 | 17.3 | *** |
| Control Diabetic Rat: | | | | | | | | |
| | 524 | 447 | 420 | 422 | 401 | 3.0 | 4.2 | |

*Transplant
**Removed transplant
***Taken for morphological analysis

Additionally, light microscopic evidence was found of the formation of new islet cells in the in situ pancreas of diabetic rats that have received a recombinant transplant. Immunocytochemical staining for insulin demonstrated insulin positive cells within the duct epithelial lining, as well as small islets forming in close association with the ducts. This indicates that the increased insulin production and secretion in the diabetic rats was due to a regeneration of pancreatic islets from ductular epithelium.

EXAMPLE 3

This example is directed toward a method of in situ regeneration of islet tissues from the host's existing unisolated pancreatic ductular epithelium by transplanting pancreatic buds or mesenchyme cells into an appropriate transplantation site. Noninbred alloxam diabetic rats were transplanted with pancreatic buds (PB) from a fetal rat, or alternatively mesenchyme (M) from a fetal rat of 11½ to 13½ days gestation. The site of the transplant was the omentum of each rat, in the vicinity of the pancreas.

Fetal pancreatic buds were obtained by dissecting the stomach-duodenal portion of a 14 day old rat fetus in 20% fetal bovine serum. The developing pancreatic bud was identified and removed from the other tissues. The isolated pancreatic bud was placed in a 95% air/5% carbon dioxide humidified atmosphere at 37 degrees C. for approximately 48 hours on a 1% bactoagar gel culture containing RPMI 1640 culture medium.

Two out of three of the diabetic rats that received a pancreatic bud transplant demonstrated reduced blood glucose values and showed elevated in situ pancreas insulin levels. One diabetic rat received a mesenchyme transplant, and also showed reduced blood glucose levels and a slight increase of in situ pancreas insulin levels.

TABLE III

| Rat # | Days | | | | | Insulin | |
|---|---|---|---|---|---|---|---|
| | 1 | 7 | 10 | 14 | 16 | ng/ml Serum | ng/mg In situ Pancreas |
| | Blood Glucose | | | mg/dl | | | |
| 53 (PB) | 646 | 435 | 408 | 450 | 415 | 2.7 | 9.3 |
| 54 (PB) | 492 | 256 | 266 | 162 | 134 | 10.4 | 31.4 |
| 58 (PB) | 418 | 74 | 76 | 89 | 78 | 1.2 | 32.2 |
| 59 (M) | 373 | 152 | 269 | 101 | 91 | 8.1 | 16.0 |
| Control Diabetic Rat: | 380 | — | — | 373 | 323 | 5.1 | 12.1 |

One added rat received a transplant of duct epithelium from a post-fetal rat, and showed no signs of normalization of diabetic symptoms.

The above has been offered for illustrative purposes only, and is not intended to limit the scope of the invention of this application, which is as defined in the claims below.

That which is claimed is:

1. A method of treating diabetes in a post-natal diabetic mammalian host which comprises: forming a recombinant, under conditions necessary for growth of mammalian cells, of fetal mesenchyme which is capable of inducing differentiation of fetal epithelial cells to form pancreatic islet tissue and (b) said diabetic's substantially pure ductal epithelium to thereby induce the formation of pancreatic islet tissue, and transplanting the pancreatic islet tissue so formed into said diabetic host at a site which supplies the necessary ingredients for growth and maintenance of the tissue.

2. The method which comprises implanting into a post-natal living subject an effective amount of fetal mesenchyme of a type and age to elicit a biological response in other fetal cells, adjacent cells of said living subject from which the biological response is to be elicited whereby said biological response is elicited in said cells wherein said biological response is the induction of cells to form desired tissues.

3. The method of claim 1 in which said fetal mesenchyme comprise pancreatic bad tissue.

4. The method of claim 2 in which said fetal mesenchyme is isolated from a human or animal fetus at such time in development when the inductive activity of the said mesenchyme is available.

5. The method of claim 2 in which fetal mesenchyme are implanted while in recombinant relationship with adult epithelial cells.

6. The method of claim 2 in which said fetal mesenchyme is implanted in the omentum of said living subject.

7. The method of claim 2 in which said biological response in said living subject is the formation of islet tissue within the in situ ductal epithelium and said fetal mesenchyme is capable of inducing differentiation of fetal epithelium into pancreatic islet tissue.

8. The method of claim 2 in which said biological response in said living subject is the formation of islet tissue within the in situ pancreas and said fetal mesenchyme is capable of inducing differentiation of fetal epithelium into pancreatic islet tissue.

9. A method of treating diabetes in a post-natal diabetic mammalian host which method comprises: implanting into a living subject, an effective amount of fetal mesenchyme of a type and age to elicit biological response in other fetal cells, adjacent ductal epithelial cells or said host whereby said biological response is elicited in said cells wherein such biological response is the formation of islet tissue.

* * * * *

UNITED STATES PATENT AND TRADEMARK OFFICE
CERTIFICATE OF CORRECTION

PATENT NO. : 4,935,000
DATED : June 19, 1990
INVENTOR(S) : Ronald W. Dudek It is certified that error appears in the above-identified patent and that said Letters Patent is hereby corrected as shown below:

IN THE CLAIMS:

Column 8, line 24, insert --(a)-- after "cells, of"

Column 8, line 39, delete "1" and insert -- 2 --

Column 8, line 40 delete "bad" and insert -- bud --

Column 8, line 63 insert -- a -- after "to elicit"

Column 8, line 65 delete "or" and insert -- of --

Signed and Sealed this

First Day of December, 1992

*Attest:*

DOUGLAS B. COMER

*Attesting Officer*  *Acting Commissioner of Patents and Trademarks*